(12) United States Patent
Park et al.

(10) Patent No.: US 8,388,856 B2
(45) Date of Patent: Mar. 5, 2013

(54) ELECTROLYTE FOR RECHARGEABLE LITHIUM BATTERY INCLUDING ADDITIVES, AND RECHARGEABLE LITHIUM BATTERY INCLUDING THE SAME

(75) Inventors: Na-Rae Park, Yongin-si (KR); Jin-Sung Kim, Yongin-si (KR); Su-Hee Han, Yongin-si (KR); Jin-Hyunk Lim, Yongin-si (KR); Mi-Hyeun Oh, Yongin-si (KR); Eun-Gi Shim, Gongju-si (KR)

(73) Assignees: Samsung SDI Co., Ltd., Gongse-dong, Giheung-gu, Yongin-si, Gyeonggi-do (KR); Techno Semichem Co., Ltd., Humax Village, Sunae-dong, Bundang-gu, Seongnam-si, Gyeonggi-do (KR)

( * ) Notice: Subject to any disclaimer, the term of this patent is extended or adjusted under 35 U.S.C. 154(b) by 0 days.

(21) Appl. No.: 12/975,148

(22) Filed: Dec. 21, 2010

(65) Prior Publication Data

US 2011/0300452 A1    Dec. 8, 2011

(30) Foreign Application Priority Data

Jun. 7, 2010   (KR) .................. 10-2010-0053460

(51) Int. Cl.
  *H01G 9/02*   (2006.01)
  *H01M 6/16*   (2006.01)
  *H01M 6/04*   (2006.01)
(52) U.S. Cl. .................. 252/62.2; 429/324; 429/199
(58) Field of Classification Search .................. None
See application file for complete search history.

(56) References Cited

U.S. PATENT DOCUMENTS

| 6,068,950 | A | 5/2000 | Gan et al. |
| 7,026,074 | B2 | 4/2006 | Chen et al. |
| 2003/0215717 | A1* | 11/2003 | Miyaki .................. 429/232 |

(Continued)

FOREIGN PATENT DOCUMENTS

JP    2006-107825 A    4/2006

(Continued)

OTHER PUBLICATIONS

Korean Office action issued by KIPO on Dec. 2, 2011, corresponding to KR Application No. 10-2010-0053460 and Request for Entry attached herewith.

(Continued)

*Primary Examiner* — Barbara Gilliam
*Assistant Examiner* — Robert S Carrico
(74) *Attorney, Agent, or Firm* — Robert E. Bushnell, Esq.

(57) ABSTRACT

An electrolyte for a rechargeable lithium battery including a non-aqueous organic solvent, a lithium salt, and an electrolyte additive including a compound represented by the following Chemical Formula 1, and a rechargeable lithium battery including the electrolyte for a rechargeable lithium battery.

[Chemical Formula 1]

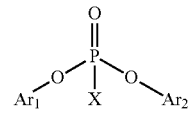

In Chemical Formula 1, $Ar_1$ and $Ar_2$ are the same or different and are independently aromatic organic groups, and X is a halogen.

11 Claims, 1 Drawing Sheet

U.S. PATENT DOCUMENTS

| | | | |
|---|---|---|---|
| 2008/0153005 A1* | 6/2008 | Horikawa et al. | 429/314 |
| 2008/0254361 A1 | 10/2008 | Horikawa | |
| 2009/0068565 A1 | 3/2009 | Lee | |
| 2009/0325065 A1 | 12/2009 | Fujii et al. | |
| 2010/0119956 A1 | 5/2010 | Tokuda et al. | |
| 2010/0159336 A1 | 6/2010 | Kim et al. | |

FOREIGN PATENT DOCUMENTS

| | | |
|---|---|---|
| JP | 2006-286570 A | 10/2006 |
| JP | 2007299542 | 11/2007 |
| JP | 2008277004 | 11/2008 |

OTHER PUBLICATIONS

Korean Notice of Allowance issued Aug. 3, 2012 in connection with Korean Patent Application Serial No. 10-2010-0053460 and Request for Entry of the Accompanying Office Action attached herewith.

* cited by examiner

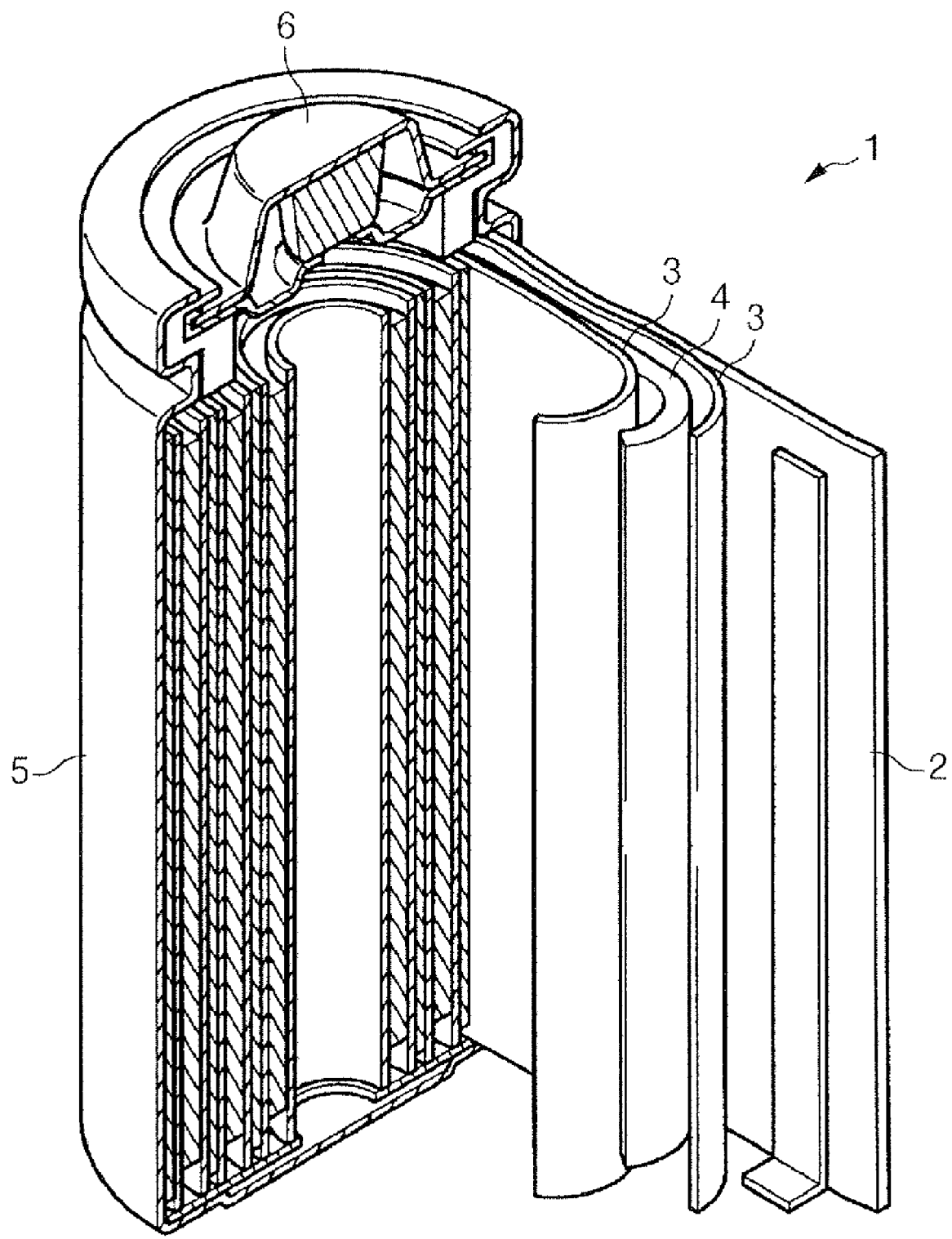

ELECTROLYTE FOR RECHARGEABLE LITHIUM BATTERY INCLUDING ADDITIVES, AND RECHARGEABLE LITHIUM BATTERY INCLUDING THE SAME

CLAIM OF PRIORITY

This application makes reference to, incorporates the same herein, and claims all benefits accruing under 35 U.S.C. §119 from an application for an ELECTROLYTE FOR RECHARGEABLE LITHIUM BATTERY INCLUDING ADDITIVES, AND RECHARGEABLE LITHIUM BATTERY INCLUDING THE SAME earlier filed in the Korean Intellectual Property Office on 7 Jun. 2010 and there duly assigned Serial No. 10-2010-0053460.

BACKGROUND OF THE INVENTION

1. Field of the Invention

This disclosure relates to an electrolyte for a rechargeable lithium battery and a rechargeable lithium battery including the same.

2. Description of the Related Art

Lithium rechargeable batteries have recently drawn attention as a power source for small portable electronic devices. They use an organic electrolyte solution and as a result have twice the discharge voltage of a conventional battery using an alkaline aqueous solution, and accordingly have a higher energy density.

As for negative active materials of a rechargeable lithium battery, various carbon-based materials such as artificial graphite, natural graphite, and hard carbon, which can all intercalate and deintercalate lithium ions, have been used.

As for positive active materials of a rechargeable lithium battery, chalcogenide compounds that are composite metal oxides such as $LiCoO_2$, $LiMn_2O_4$, $LiNiO_2$, $LiNi_{1-x}Co_xO_2$ ($0<x<1$), $LiMnO_2$, $Li[NiCoMn]O_2$, and the like, are used. For an electrolyte, a lithium salt dissolved in a non-aqueous solvent including ethylene carbonate, dimethyl carbonate, diethyl carbonate, and the like has been used.

During initial charge of a rechargeable lithium battery, lithium ions, which are released from the lithium-transition metal oxide positive electrode of the battery, are transferred to a carbon-based negative electrode where the ions are intercalated into the carbon.

Because of its high reactivity, lithium reacts with the carbon-based negative electrode to produce $Li_2CO_3$, LiO, LiOH, etc., thereby forming a thin film on the surface of the negative electrode. This film is referred to as an organic solid electrolyte interface (SEI) film. The organic SEI film formed during the initial charge not only prevents the reaction between lithium ions and the carbon-based negative electrode or other materials during charging and discharging, but it also acts as an ion tunnel, allowing the passage of only lithium ions.

The ion tunnel prevents the disintegration of the structure of the carbon negative electrode, which causes organic solvents in an electrolyte with a high molecular weight to make solvate lithium ions, and the solvent and the solvated lithium ions co-intercalate into the carbon-based negative electrode. Once the organic SEI film is formed, lithium ions do not again react with the carbon electrode or other materials such that the amount of lithium ions is reversibly maintained.

However, problems may occur in which gases are generated inside a battery using carbonate-based organic solvents due to decomposition of a carbonate-based organic solvent during the organic SEI film-forming reaction. These gases include $H_2$, CO, $CO_2$, $CH_4$, $C_2H_6$, $C_3H_8$, $C_3H_6$, etc., depending on the type of non-aqueous organic solvent and negative active material used.

Due to gas generation inside the battery, the battery may expand during charge. In addition, an SEI film is slowly disintegrated by electrochemical energy and heat energy, which increases with the passage of time when the fully charged battery is stored at a high temperature after it is charged, for example, if it is stored at 85° C. for four days after a 100% charge at 4.2 V.

Accordingly, a side reaction in which an exposed surface of the negative electrode reacts with surrounding electrolyte occurs continuously to generate gases. The internal pressure of the battery increases with this generation of gases. Therefore, what is needed is the development of an electrolyte additive that suppresses a volume expansion of the rechargeable lithium battery by preventing or reducing this generation of gases during SEI film-forming reactions.

SUMMARY OF THE INVENTION

One aspect of the present invention provides an electrolyte for a rechargeable lithium battery that may suppress the volume expansion of rechargeable lithium battery at room temperature and at a high temperature.

Another aspect of the present invention provides a rechargeable lithium battery including the electrolyte for a rechargeable lithium battery.

According to one aspect, an electrolyte for a rechargeable lithium battery is provided that includes a non-aqueous organic solvent, a lithium salt, and an electrolyte additive including a compound represented by the following Chemical Formula 1:

[Chemical Formula 1]

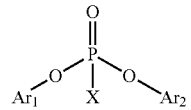

In Chemical Formula 1, $Ar_1$ and $Ar_2$ are the same or different, and are independently aromatic organic groups, and X is a halogen, for example fluorine (F) or chlorine (Cl).

The additive for an electrolyte for a rechargeable lithium battery may include the compound represented by the following Chemical Formula 2:

[Chemical Formula 2]

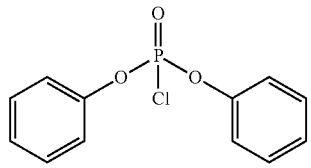

The electrolyte additive may be included at about 0.1 to about 5 wt % based on the total amount of the electrolyte.

The electrolyte additive for a rechargeable lithium battery may further include a vinylene carbonate-based compound, an ethylene carbonate-based compound represented by the following Chemical Formula 3, or a combination thereof.

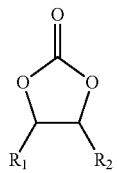

[Chemical Formula 3]

In Chemical Formula 3, R1 and R2 are independently selected from hydrogen, a halogen, a cyano group (CN), a nitro group ($NO_2$), or a C1 to C5 fluoroalkyl group, provided that both $R_1$ and $R_2$ are not hydrogen.

Another aspect of the present invention provides a rechargeable lithium battery that includes a positive electrode including a positive active material, a negative electrode including a negative active material, and the above electrolyte.

The positive active material may be selected from the compounds represented by the following formulae. $Li_aA_{1-b}X_bD_2$ ($0.90 \leq a \leq 1.8$ and $0 \leq b \leq 0.5$); $Li_aA_{1-b}X_bO_{2-c}D_c$ ($0.90 \leq a \leq 1.8$, $0 \leq b \leq 0.5$, and $0 \leq c \leq 0.05$); $Li_aE_{1-b}X_bO_{2-c}D_c$ ($0.90 \leq a \leq 1.8$, $0 \leq b \leq 0.5$ and $0 \leq c \leq 0.05$); $Li_aE_{2-b}X_bO_{4-c}D_c$ ($0.90 \leq a \leq 1.8$, $0 \leq b \leq 0.5$ and $0 \leq c \leq 0.05$); $Li_aNi_{1-b-c}Co_bX_cD_\alpha$ ($0.90 \leq a \leq 1.8$, $0 \leq b \leq 0.5$, $0 \leq c \leq 0.05$, and $0 < \alpha \leq 2$); $Li_aNi_{1-b-c}Co_bX_cO_{2-\alpha}T_\alpha$ ($0.90 \leq a \leq 1.8$, $0 \leq b \leq 0.5$, $0 \leq c \leq 0.05$, and $0 < \alpha < 2$); $Li_aNi_{1-b-c}Co_bX_cO_{2-\alpha}T_2$ ($0.90 \leq a \leq 1.8$, $0 \leq b \leq 0.5$, $0 \leq c \leq 0.05$, and $0 < \alpha < 2$); $Li_aNi_{1-b-c}Mn_bX_cD_\alpha$ ($0.90 \leq a \leq 1.8$, $0 \leq b \leq 0.5$, $0 \leq c \leq 0.05$, and $0 < \alpha < 2$); $Li_aNi_{1-b-c}Mn_bX_cO_{2-\alpha}T_\alpha$ ($0.90 \leq a \leq 1.8$, $0 \leq b \leq 0.5$, $0 \leq c \leq 0.05$, and $0 < \alpha < 2$); $Li_aNi_{1-b-c}Mn_bX_cO_{2-\alpha}T_2$ ($0.90 \leq a \leq 1.8$, $0 \leq b \leq 0.5$, $0 \leq c \leq 0.05$, and $0 < \alpha < 2$); $Li_aNi_bE_cG_dO_2$ ($0.90 \leq a \leq 1.8$, $0 \leq b \leq 0.9$, $0 \leq c \leq 0.5$, and $0.001 \leq d \leq 0.1$); $Li_aNi_bCo_cMn_dG_eO_2$ ($0.90 \leq a \leq 1.8$, $0 \leq b \leq 0.9$, $0 \leq c \leq 0.5$, $0 \leq d \leq 0.5$, and $0.001 \leq e \leq 0.1$); $Li_aNiG_bO_2$ ($0.90 \leq a \leq 1.8$ and $0.001 \leq b \leq 0.1$); $Li_aCoG_bO_2$ ($0.90 \leq a \leq 1.8$ and $0.001 \leq b \leq 0.1$); $Li_aMnG_bO_2$ ($0.90 \leq a \leq 1.8$ and $0.001 \leq b \leq 0.1$); $Li_aMn_2G_bO_4$ ($0.90 \leq a \leq 1.8$ and $0.001 \leq b \leq 0.1$); $Li_aMnG_bPO_4$ ($0.90 \leq a \leq 1.8$ and $0.001 \leq b \leq 0.1$); $QO_2$; $QS_2$; $LiQS2$; $V_2O_5$; $LiV_2O_5$; $LiZO_2$; $LiNiVO_4$; $Li_{(3-f)}J_2(PO_4)_3$ ($0 \leq f \leq 2$); $Li_{(3-f)}Fe_2(PO_4)_3$ ($0 \leq f \leq 2$); and $LiFePO_4$.

In the above Chemical Formulae, A is selected from a group consisting of Ni, Co, Mn, and a combination thereof; X is selected from a group consisting of Al, Ni, Co, Mn, Cr, Fe, Mg, Sr, V, a rare earth element, and a combination thereof; D is selected from a group consisting of O, F, S, P, and a combination thereof; E is selected from a group consisting of Co, Mn, and a combination thereof; T is selected from a group consisting of F, S, P, and a combination thereof; G is selected from a group consisting of Al, Cr, Mn, Fe, Mg, La, Ce, Sr, V, and a combination thereof; Q is selected from a group consisting of Ti, Mo, Mn, and a combination thereof; Z is selected from a group consisting of Cr, V, Fe, Sc, Y, and a combination thereof; and J is selected from a group consisting of V, Cr, Mn, Co, Ni, Cu, and a combination thereof.

In one embodiment, for the positive active material, a lithium nickel cobalt manganese-based compound is exemplified. The lithium nickel cobalt manganese-based compound may be represented by formula $Li_xMO_{2-z}L_z$, wherein M is $M'_{1-k}A_k$, where A is a dopant such as B, Ca, Zr, S, F, P, Bi, Al, Mg, Zn, Sr, Cu, Fe, Ga, In, Cr, Ge or Sn, $0 \leq k < 0.05$, and M' is $Ni_{1-d-e}Mn_dCo_e$, where $0.65 \leq d+e \leq 0.85$, $0.1 \leq e \leq 0.4$; L is selected from a group consisting of F, S, P and combinations thereof; $0.95 \leq x \leq 1.05$; and $0 \leq z \leq 2$.

According to one embodiment of the present invention, the electrolyte for a rechargeable lithium battery including the electrolyte additive for a rechargeable lithium battery improves the storage characteristics at room temperature and at a high temperature, so the rechargeable lithium battery including the same improves storage characteristics at room temperature and at a high temperature.

BRIEF DESCRIPTION OF THE DRAWING

The above and other features and advantages of the present invention will become more apparent by describing in detail exemplary embodiments thereof with reference to the attached drawings in which:

FIG. 1 is a schematic view of a rechargeable lithium battery according to one embodiment of the present invention.

DETAILED DESCRIPTION OF THE INVENTION

Exemplary embodiments of the present invention will hereinafter be described in detail. However, these embodiments are only exemplary, and the present invention is not limited thereto.

Unless mentioned otherwise in the specification, the term "aromatic organic group" indicates to C6 to C30 aryl group or a C2 to C30 hetero aryl group, for example, a C6 to C16 aryl group or a C2 to C16 hetero aryl group, and the term "halogen" indicates F, Cl, Br, or I. Unless mentioned otherwise in the specification, the term "hetero aryl group" indicates an aryl group having 1 to 3 hetero atoms of N, O, S, Si, or P, and carbons at other sites in one ring.

According to one embodiment, an electrolyte for a rechargeable lithium battery is provided that includes a non-aqueous organic solvent, a lithium salt, and an electrolyte additive including a compound represented by the following Chemical Formula 1:

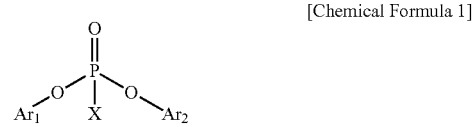

[Chemical Formula 1]

In Chemical Formula 1, $Ar_1$ and $Ar_2$ are the same or are different, and are independently aromatic organic groups, and X is a halogen, for example fluorine (F) or chlorine (Cl). For example, the electrolyte additive for a rechargeable lithium battery may include a compound represented by the following Chemical Formula 2:

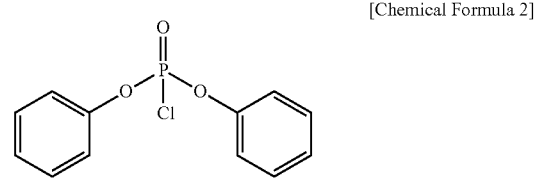 [SMILES: O=P(Cl)(Oc1ccccc1)Oc1ccccc1]

[Chemical Formula 2]

When the electrolyte includes the electrolyte additive for a rechargeable lithium battery that includes a compound represented by Chemical Formula 1, for example a compound represented by Chemical Formula 2, as well as a carbonate-based organic solvent, the electrolyte additive for a rechargeable lithium battery may be decomposed prior to the carbonate-based organic solvent.

As a result, the electrolyte additive may suppress the decomposition of the non-aqueous organic solvent such as ethylene carbonate, dimethyl carbonate, or the like, and may suppress the gas generation due to the decomposition of the carbonate-based organic solvent. As a result, the electrolyte additive may suppress the volume expansion and the internal pressure increase of the rechargeable lithium battery.

Furthermore, the electrolyte additive for a rechargeable lithium battery may be included at about 0.1 to about 5 wt % based on the total weight of the electrolyte. When the electrolyte additive for a rechargeable lithium battery is included within this range, it may effectively suppress the volume expansion and the internal pressure increase of the rechargeable lithium battery, so as to improve the stability of the rechargeable lithium battery. For example, the electrolyte additive for a rechargeable lithium battery may be included at about 0.1 to about 3 wt % based on the total amount of the electrolyte.

The electrolyte may further include vinylene carbonate-based compound, an ethylene carbonate-based compound of the following Chemical Formula 3, or a combination thereof, in order to improve the cycle life of a battery.

[Chemical Formula 3]

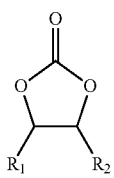

In Chemical Formula 3, R1 and R2 are independently selected from hydrogen, a halogen, a cyano group (CN), a nitro group ($NO_2$), or a C1 to C5 fluoroalkyl group, provided that both $R_1$ and $R_2$ are not hydrogen.

Examples of the ethylene carbonate-based compound include difluoroethylene carbonate, chloroethylene carbonate, dichloroethylene carbonate, bromoethylene carbonate, dibromoethylene carbonate, nitroethylene carbonate, cyanoethylene carbonate, fluoroethylene carbonate, and a combination thereof. In one embodiment, fluoroethylene carbonate is desirable.

Example of the vinylene carbonate-based compound may include vinylene carbonate. The vinylene carbonate-based compound and the ethylene carbonate-based compound provide the negative electrode with a stable SEI film. As a result, the SEI film is not broken and is well maintained, even if the lithium ions are repeatedly transmitted during charging and discharging, so that the charge and discharge capacity can be effectively maintained. Resultantly, the rechargeable lithium battery including the same may effectively improve the cycle-life characteristics. Furthermore, the amounts of these compounds may be controlled to improve the cycle life.

In an electrolyte for a rechargeable lithium battery according to one embodiment of the present invention, a non-aqueous organic solvent serves as a medium for transmitting ions that participate in the electrochemical reaction of the battery. The non-aqueous organic solvent includes a carbonate-based solvent. Furthermore, the non-aqueous organic solvent may further include ester-based, ether-based, ketone-based, alcohol-based, or aprotic solvent, but is not limited thereto.

Examples of the carbonate-based solvent may include dimethyl carbonate (DMC), diethyl carbonate (DEC), dipropyl carbonate (DPC), methylpropyl carbonate (MPC), ethylpropyl carbonate (EPC), ethylmethyl carbonate (EMC), ethylene carbonate (EC), propylene carbonate (PC), butylene carbonate (BC), and the like. Examples of the ester-based solvent may include methylacetate, ethylacetate, n-propylacetate, dimethylacetate, methylpropionate, ethylpropionate, γ-butyrolactone, decanolide, valerolactone, mevalonolactone, caprolactone, and the like. Examples of the ether-based solvent include dimethyl ether, dibutyl ether, tetraglyme, diglyme, dimethoxyethane, 2-methyltetrahydrofuran, tetrahydrofuran (THF), and the like. Examples of the ketone-based solvent include cyclohexanone and the like. Examples of the alcohol-based solvent include ethyl alcohol, isopropyl alcohol, and the like. Examples of the aprotic solvent include nitriles such as R—CN (where R is a C2 to C20 chain, branched, or cyclic hydrocarbon, a double bond, an aromatic ring, or an ether bond), amides such as dimethyl formamide (DMF), dimethyl acetamide (DMAC), dioxolanes such as 1,3-dioxolane, sulfolanes, cycloalkanes such as cyclohexane, and the like.

The non-aqueous organic solvent may be used singularly or in a mixture. When the organic solvent is used in a mixture, the mixture ratio can be controlled in accordance with a desirable battery performance.

The carbonate-based solvent may include a mixture of a cyclic carbonate and a chain carbonate. The cyclic carbonate and the chain carbonate are mixed together in a volume ratio of about 1:1 to about 1:9. When a mixture is used as an electrolyte, the electrolyte performance may be enhanced.

In addition, the non-aqueous organic electrolyte may further include the mixture of a carbonate-based solvent and an aromatic hydrocarbon-based solvent. The carbonate-based solvent and the aromatic hydrocarbon-based solvent may be mixed together in a volume ratio ranging from about 1:1 to about 30:1. The aromatic hydrocarbon-based organic solvent may be represented by the following Chemical Formula 4:

[Chemical Formula 4]

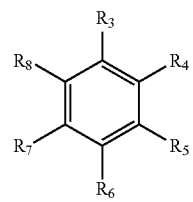

In Chemical Formula 4, $R_3$ to $R_8$ are the same or different, and are independently hydrogen, a halogen, a C1 to C10 alkyl group, a C1 to C10 haloalkyl group, or a combination thereof.

The aromatic hydrocarbon-based organic solvent may include, but is not limited to, at least one selected from benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 1,2-difluorotoluene, 1,3-difluorotoluene, 1,4-difluorotoluene, 1,2,3-trifluorotoluene, 1,2,4-trifluorotoluene, chlorotoluene, 1,2-dichlorotoluene, 1,3-dichlorotoluene, 1,4-dichlorotoluene, 1,2,3-trichlorotoluene, 1,2,4-trichlorotoluene, iodotoluene, 1,2-diiodotoluene, 1,3-diiodotoluene, 1,4-diiodotoluene, 1,2,3-triiodotoluene, 1,2,4-triiodotoluene, xylene, or a combination thereof.

The lithium salt is dissolved in an organic solvent, supplies lithium ions in the battery, operates a basic operation of a rechargeable lithium battery, and improves lithium ion transport between positive and negative electrodes. Examples of the lithium salt include at least one supporting salt selected from $LiPF_6$, $LiBF_4$, $LiSbF_6$, $LiAsF_6$, $LiCF_3SO_3$, $LiN(SO_2C_2F_5)_2$, $Li(CF_3SO_2)_2N$, $LiN(SO_3C_2F_5)_2$, $LiC_4F_9SO_3$, $LiClO_4$, $LiAlO_4$, $LiAlO_2$, $LiAlCl_4$, $LiN(C_xF_{2x+1}SO_2)(C_yF_{2y+1}SO_2)$ (where x and y are natural numbers), LiCl, LiI, $LiB(C_2O_4)_2$ (lithium bisoxalato borate: LiBOB), and a combination thereof. The lithium salt may be used in a concentration ranging from about 0.1 M to about 2.0 M, and in one embodiment, at about 0.5 M to about 2.0 M. When the lithium salt is included at the above concentration range, electrolyte performance and lithium ion mobility may be enhanced due to optimal electrolyte conductivity and viscosity.

According to another embodiment of the present invention, a rechargeable lithium battery is provided that includes a positive electrode including a positive active material, a negative electrode including a negative active material, and the above-described electrolyte. The positive electrode includes a current collector and a positive active material layer including a positive active material positioned on the current collector.

The positive active material includes lithiated intercalation compounds that reversibly intercalate and deintercalate lithium ions. The positive active material may include a composite oxide including at least one selected from a group consisting of cobalt, manganese, and nickel, as well as lithium. In one embodiment, the following lithium-containing compounds may be used, but it is not limited thereto: $Li_aA_{1-b}X_bD_2$ ($0.90 \leq a \leq 1.8$ and $0 \leq b \leq 0.5$); $Li_aA_{1-b}X_bO_{2-c}D_2$ ($0.90 \leq a \leq 1.8$, $0 \leq b \leq 0.5$, and $0 \leq c \leq 0.05$); $Li_aE_{1-b}X_bO_{2-c}D_c$ ($0.90 \leq a \leq 1.8$, $0 \leq b \leq 0.5$ and $0 \leq c \leq 0.05$); $Li_aE_{2-b}X_bO_{4-c}D_c$ ($0.90 \leq a \leq 1.8$, $0 \leq b \leq 0.5$ and $0 \leq c \leq 0.05$); $Li_aNi_{1-b-c}Co_bX_cD_\alpha$ ($0.90 \leq a \leq 1.8$, $0 \leq b \leq 0.5$, $0 \leq c \leq 0.05$, and $0 < \alpha \leq 2$); $Li_aNi_{1-b-c}Co_bX_cO_{2-\alpha}T_\alpha$ ($0.90 \leq a \leq 1.8$, $0 \leq b \leq 0.5$, $0 \leq c \leq 0.05$, and $0 < \alpha < 2$); $Li_aNi_{1-b-c}Co_bX_cO_{2-\alpha}T_2$ ($0.90 \leq a \leq 1.8$, $0 \leq b \leq 0.5$, $0 \leq c \leq 0.05$, and $0 < \alpha < 2$); $Li_aNi_{1-b-c}Mn_bX_cD_\alpha$ ($0.90 \leq a \leq 1.8$, $0 \leq b \leq 0.5$, $0 \leq c \leq 0.05$, and $0 < \alpha \leq 2$); $Li_aNi_{1-b-c}Mn_bX_cO_{2-\alpha}T_\alpha$ ($0.90 \leq a \leq 1.8$, $0 \leq b \leq 0.5$, $0 \leq c \leq 0.05$, and $0 < \alpha < 2$); $Li_aNi_{1-b-c}Mn_bX_cO_{2-\alpha}T_2$ ($0.90 \leq a \leq 1.8$, $0 \leq b \leq 0.5$, $0 \leq c \leq 0.05$, and $0 < \alpha < 2$); $Li_aNi_bE_cG_dO_2$ ($0.90 \leq a \leq 1.8$, $0 \leq b \leq 0.9$, $0 \leq c \leq 0.5$, and $0.001 \leq d \leq 0.1$); $Li_aNi_bCo_cMn_dG_eO_2$ ($0.90 \leq a \leq 1.8$, $0 \leq b \leq 0.9$, $0 \leq c \leq 0.5$, $0 \leq d \leq 0.5$, and $0.001 \leq e \leq 0.1$); $Li_aNiG_bO_2$ ($0.90 \leq a \leq 1.8$, $0.001 \leq b \leq 0.1$); $Li_aCoG_bO_2$ ($0.90 \leq a \leq 1.8$ and $0.001 \leq b \leq 0.1$); $Li_aMnG_bO_2$ ($0.90 \leq a \leq 1.8$ and $0.001 \leq b \leq 0.1$); $Li_aMn_2G_bO_4$ ($0.90 \leq a \leq 1.8$ and $0.001 \leq b \leq 0.1$); $Li_aMnG_bPO_4$ ($0.90 \leq a \leq 1.8$ and $0.001 \leq b \leq 0.1$); $QO_2$; $QS_2$; $LiQS_2$; $V_2O_5$; $LiV_2O_5$; $LiZO_2$; $LiNiVO_4$; $Li_{(3-f)}J_2(PO_4)_3$ ($0 \leq f \leq 2$); $Li_{(3-f)}Fe_2(PO_4)_3$ ($0 \leq f \leq 2$); and $LiFePO_4$.

In the above Chemical Formulae, A is selected from a group consisting of Ni, Co, Mn, and a combination thereof; X is selected from a group consisting of Al, Ni, Co, Mn, Cr, Fe, Mg, Sr, V, a rare earth element, and a combination thereof; D is selected from a group consisting of O, F, S, P, and a combination thereof; E is selected from a group consisting of Co, Mn, and a combination thereof; T is selected from a group consisting of F, S, P, and a combination thereof; G is selected from a group consisting of Al, Cr, Mn, Fe, Mg, La, Ce, Sr, V, and a combination thereof; Q is selected from a group consisting of Ti, Mo, Mn, and a combination thereof; Z is selected from a group consisting of Cr, V, Fe, Sc, Y, and a combination thereof; and J is selected from a group consisting of V, Cr, Mn, Co, Ni, Cu, and a combination thereof.

In one embodiment, for the positive active material, a lithium nickel cobalt manganese-based oxide is exemplified. The lithium nickel cobalt manganese-based compound may be represented by formula $Li_xMO_{2-z}L_z$, wherein M is $M'_{1-k}A_k$, where A is a dopant such as B, Ca, Zr, S, F, P, Bi, Al, Mg, Zn, Sr, Cu, Fe, Ga, In, Cr, Ge or Sn, $0 \leq k < 0.05$, and M' is $Ni_{1-d-e}Mn_dCo_e$, where $0.65 \leq d+e \leq 0.85$, $0.1 \leq e \leq 0.4$; L is selected from a group consisting of F, S, P and combinations thereof; $0.95 \leq x \leq 1.05$; and $0 \leq z \leq 2$.

When the positive active material includes a lithium nickel cobalt manganese-based oxide, the rechargeable lithium battery including the electrolyte additive may further effectively suppress the volume expansion and the internal pressure increase of a rechargeable lithium battery.

The positive active material may include the positive active material with the coating layer, or a compound of the active material and the active material coated with the coating layer. The coating layer may include at least one coating element compound selected from a group consisting of an oxide of the coating element, a hydroxide of the coating element, an oxyhydroxide of the coating element, an oxycarbonate of the coating element, and a hydroxycarbonate of the coating element. The compound for the coating layer may be either amorphous or crystalline. The coating element included in the coating layer may be selected from a group consisting of Mg, Al, Co, K, Na, Ca, Si, Ti, V, Sn, Ge, Ga, B, As, Zr, and combinations thereof. The coating process may include any conventional process as long as it does not cause any side effects to the properties of the positive active material (e.g., spray coating, immersing), which is well known to persons having ordinary skill in this art, so a detailed description thereof is omitted.

The positive active material layer further includes a binder and a conductive material. The binder improves binding properties of the positive active material particles to each other and to a current collector. Examples of the binder include at least one selected from a group consisting of polyvinyl alcohol, carboxylmethyl cellulose, hydroxypropyl cellulose, diacetyl cellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, styrene-butadiene rubber, acrylated styrene-butadiene rubber, an epoxy resin, nylon, and the like, but is not limited thereto.

The conductive material improves electrical conductivity of a negative electrode. Any electrically conductive material can be used as a conductive agent unless it causes a chemical change. Examples of the conductive material include at least one selected from natural graphite, artificial graphite, carbon black, Super-P (3M company), acetylene black, ketjen black, hard carbon (carbon obtained through sintering at a high temperature), soft carbon (carbon obtained through sintering at a low temperature), carbon fiber, a metal powder or a metal fiber including copper, nickel, aluminum, silver, and the like, polyphenylene derivatives, and the like. The current collector may be Al, but is not limited thereto.

The negative electrode includes a current collector and a negative active material layer disposed thereon. The negative active material layer includes a negative active material.

The negative active material includes a material that reversibly intercalates/deintercalates lithium ions, a lithium metal, a lithium metal alloy, a material being capable of doping lithium, or a transition metal oxide.

The material that can reversibly intercalate/deintercalate lithium ions includes a carbon material. The carbon material may be any generally-used carbon-based negative active material in a lithium ion rechargeable battery. Examples of the carbon material include crystalline carbon, amorphous carbon, and mixtures thereof. The crystalline carbon may be shapeless, sheet, flake, spherical, or fiber shaped natural graphite or artificial graphite. The amorphous carbon may be a soft carbon, a hard carbon, mesophase pitch carbide, fired coke, and the like.

Examples of the lithium metal alloy include lithium and a metal selected from a group consisting of Na, K, Rb, Cs, Fr, Be, Mg, Ca, Sr, Si, Sb, Pb, In, Zn, Ba, Ra, Ge, Al, Sn, Ti, Ag, Cd, Ga, Bi, and a combination thereof.

Examples of the material being capable of doping lithium include Si, $SiO_x$ ($0<x<2$), a Si-Q alloy (where Q is an element selected from a group consisting of an alkali metal, an alkaline-earth metal, a group 13 element, a group 14 element, a transition element, a rare earth element, and combinations thereof, and is not Si), Sn, $SnO_2$, a Sn—R alloy (where R is an element selected from a group consisting of an alkali metal, an alkaline-earth metal, a group 13 element, a group 14 element, a transition element, a rare earth element, and combinations thereof, and is not Sn), or mixtures thereof. At least one of these materials may be mixed with $SiO_2$. In addition, carbon may further be deposited on the surface of the material being capable of doping lithium. Coating the surface of the above materials with carbon may be performed by decomposing such organic materials as ethylene, tetrahydrofuran (THF), and cyclohexanone at a high temperature of 800° C. or higher in a vacuum in the presence of the above materials, but is not limited thereto. The elements Q and R may be selected from a group consisting of Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Ti, Ge, P, As, Sb, Bi, S, Se, Te, Po, and a combination thereof.

Examples of the transition metal oxide include vanadium oxide, lithium vanadium oxide, and the like.

The negative active material layer includes a binder, and optionally a conductive material. The binder improves binding properties of negative active material particles to one another and to a current collector. The binder may include a non-water-soluble binder, a water-soluble binder, or a combination thereof.

Examples of the non-water-soluble binder include polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, polyamideimide, polyimide, and a combination thereof.

The water-soluble binder includes a styrene-butadiene rubber, an acrylated styrene-butadiene rubber, polyvinyl alcohol, sodium polyacrylate, a copolymer including propylene and a C2 to C8 olefin, a copolymer of (meth)acrylic acid and (meth) acrylic acid alkyl ester, or a combination thereof.

When the water-soluble binder is used as a negative electrode binder, a cellulose-based compound may be further used to provide viscosity. The cellulose-based compound includes one or more of carboxylmethyl cellulose, hydroxypropylmethyl cellulose, methyl cellulose, or alkaline metal salts thereof. The alkaline metal may be sodium (Na), potassium (K), or lithium (Li). The cellulose-based compound may be included in an amount of 0.1 to 3 parts by weight based on 100 parts by weight of the binder.

The conductive material is included to improve electrode conductivity. Any electrically conductive material may be used as a conductive material unless it causes a chemical change. Examples of the conductive material include carbon-based materials such as natural graphite, artificial graphite, carbon black, Super-P (3M company), acetylene black, ketjen black, hard carbon, soft carbon, carbon fiber, and the like, metal-based materials such as a metal powder or a metal fiber including copper, nickel, aluminum, silver, and the like, conductive polymers such as polyphenylene derivatives, or mixtures thereof.

The current collector may be selected from a group consisting of a copper foil, a nickel foil, a stainless steel foil, a titanium foil, a nickel foam, a copper foam, a polymer substrate coated with a conductive metal, and combinations thereof.

The positive and negative electrodes may be fabricated by a method including mixing the active material, a conductive material, and a binder into an active material composition and coating the composition on a current collector. The electrode manufacturing method is well known, and thus is not described in detail in the present specification. The solvent can be N-methylpyrrolidone, but it is not limited thereto.

The rechargeable lithium battery may further include a separator between the negative electrode and the positive electrode, as needed. Non-limiting examples of suitable separator materials include polyethylene, polypropylene, polyvinylidene fluoride, and multi-layers thereof, such as a polyethylene/polypropylene double-layered separator, a polyethylene/polypropylene/polyethylene triple-layered separator, and a polypropylene/polyethylene/polypropylene triple-layered separator.

Rechargeable lithium batteries may be classified as lithium ion batteries, lithium ion polymer batteries, and lithium polymer batteries according to the presence of a separator and the kind of electrolyte used therein. The rechargeable lithium batteries may have a variety of shapes and sizes, and include cylindrical, prismatic, coin, or pouch-type batteries, and may be thin film batteries, or may be rather bulky in size. Structures and fabricating methods for lithium ion batteries pertaining to the present invention are well known in the art.

Turning now to FIG. 1, FIG. 1 provides a schematic view showing the representative structure of a rechargeable lithium battery according to one embodiment. Referring to FIG. 1, a cylindrical lithium battery 1 includes a negative electrode 2, a positive electrode 4, a separator 3 interposed between the negative electrode 2 and positive electrode 4, a battery case 5, and a sealing member 6. The shape of the rechargeable lithium battery in accordance with the present invention is not limited to the above, and may instead be of other and diverse forms such as a prismatic form, a pouch form, a coin-type form, as long as the rechargeable lithium battery includes the additive-containing electrolyte for a rechargeable lithium battery and operates as a battery.

The following examples illustrate the present invention in more detail. These examples, however, should not in any sense be interpreted as limiting the scope of the present invention.

EXAMPLES

Preparation of Electrolyte

Preparation Example 1

Ethylene carbonate, ethylmethyl carbonate, and diethyl carbonate are mixed in a weight ratio of 1:1:1 (ethylene carbonate:ethylmethyl carbonate:diethyl carbonate) and added with $LiPF_6$ in a concentration of 1.0 M. As an additive, the compound represented by the following Chemical Formula 2 is added thereto at 0.5 wt % based on the total weight of electrolyte to provide an electrolyte.

[Chemical Formula 2]

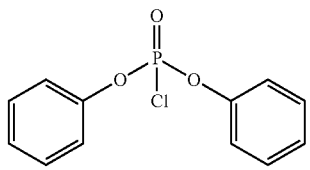

Preparation Example 2

An electrolyte is prepared in accordance with the same procedure as in Preparation Example 1, except that the compound represented by Chemical Formula 2 is added as an additive at 1 wt % based on the total weight of the electrolyte.

Preparation Example 3

An electrolyte is prepared in accordance with the same procedure as in Preparation Example 1, except that the compound represented by the Chemical Formula 2 is added as an additive at 3 wt % based on the total weight of the electrolyte.

Preparation Example 4

An electrolyte is prepared in accordance with the same procedure as in Preparation Example 1, except that the compound represented by the Chemical Formula 2 is added as an additive at 5 wt % based on the total weight of the electrolyte.

Preparation Example 5

An electrolyte is prepared in accordance with the same procedure as in Preparation Example 1, except that the additive is not added.

Fabricating Rechargeable Lithium Battery

Example 1 to Example 4

A lithium nickel cobalt manganese-based oxide of $LiNi_{0.5}Co_{0.2}Mn_{0.3}O_2$, a polyvinylidene fluoride (PVDF) binder, and carbon black are mixed in a weight ratio of 92:4:4 ($LiNi_{0.5}Co_{0.2}Mn_{0.3}O_2$:polyvinylidene fluoride:carbon black) in a solvent of N-methylpyrrolidone in order to provide a positive active material slurry. The positive active material slurry is uniformly coated on an aluminum current collector having a thickness of 20 µm and is dried and pressed to provide a positive electrode.

A crystalline artificial graphite and polyvinylidene fluoride (PVDF) binder are mixed in a weight ratio of 92:8 (crystalline artificial graphite:polyvinylidene fluoride) in an N-methylpyrrolidone solvent to provide a negative active material slurry. The negative active material slurry is uniformly coated on a copper current collector having a thickness of 15 µm and dried and pressed to provide a negative electrode.

Using the obtained positive electrode and negative electrode, and the electrolyte obtained from each of Preparation Example 1 to Preparation Example 4, a prismatic cell according to Examples 1 to 4 having dimensions of 30 mm×48 mm×6 mm is fabricated according to the general method.

Comparative Example 1

Using the positive electrode and negative electrode obtained from each of Example 1, and the electrolyte obtained from Preparation Example 5, a 30 mm×48 mm×6 mm prismatic cell according to Comparative Example 1 is fabricated according to the general method.

Assessment of Storage Characteristics at High Temperature

The cells obtained from Example 1 to Example 4 and Comparative Example 1 are charged at 0.5C in 4.2 V to 4.35 V and are allowed to stand in an oven at 85° C. for 5 hours. Then each is measured for thickness to determine the thickness increase ratio with regard to the initial thickness. The results are shown in the following Table 1.

In addition, the cell after being allowed to stand at a high temperature is discharged at 0.5C to 3.2V, and the capacity retention (%, (discharge capacity/standard charge capacity) *100) is calculated. The results are shown in the following Table 1.

TABLE 1

| | Thickness increase ratio after storage at a high temperature (%) | Capacity retention after storage at a high temperature (%) |
|---|---|---|
| Example 1 | 12 | 81 |
| Example 2 | 10 | 82 |
| Example 3 | 8 | 84 |
| Example 4 | 13 | 80 |
| Comparative Example 1 | 21 | 75 |

As shown in Table 1, the thickness of each rechargeable lithium cell obtained from Example 1 to Example 4 is increased by 8% to 13% after being allowed to stand at 85° C. for 5 hours, so it is confirmed that the rechargeable lithium battery according to the present invention effectively suppresses the volume expansion and the internal pressure increase. On the other hand, the rechargeable lithium battery according to Comparative Example 1 increases in thickness by 21%, so it is confirmed that the rechargeable lithium battery deteriorates due to the volume expansion and the internal pressure increase.

In addition, the rechargeable lithium cells obtained from Example 1 to Example 4 show capacity retention of 80% to 84% after being allowed to stand at 85° C. for 5 hours, which confirms that the capacity is effectively maintained after storage at a high temperature. On the other hand, the rechargeable lithium cell obtained from Comparative Example 1 shows capacity retention of 75% after being allowed to stand at 85° C. for 5 hours, which confirms that the capacity retention deteriorates after storage at a high temperature.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An electrolyte for a rechargeable lithium battery, comprising:
   a non-aqueous organic solvent;
   a lithium salt; and
   an electrolyte additive including a compound represented by the following Chemical Formula 1:

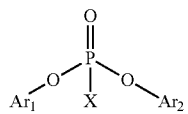

[Chemical Formula 1]

wherein, $Ar_1$ and $Ar_2$ are the same or different, and are independently aromatic organic groups, and X is a halogen, wherein the electrolyte additive is included at 0.1 to 3 wt % based on the total amount of electrolyte.

2. The electrolyte for a rechargeable lithium battery of claim 1, wherein X is an element selected from a group consisting of fluorine (F) and chlorine (Cl).

3. The electrolyte of claim 1, wherein X is chlorine (Cl).

4. The electrolyte of claim 1, wherein the electrolyte additive comprises a compound represented by the following Chemical Formula 2:

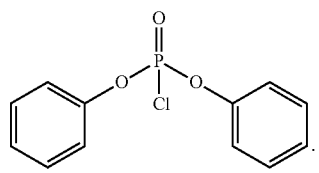

[Chemical Formula 2]

5. A rechargeable lithium battery, comprising:
a positive electrode comprising a positive active material;
a negative electrode comprising a negative active material; and
an electrolyte comprising a non-aqueous organic solvent; a lithium salt; and an electrolyte additive comprising a compound represented by the following Chemical Formula 1:

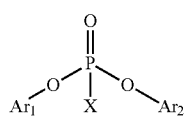

[Chemical Formula 1]

wherein, $Ar_1$ and $Ar_2$ are the same or different, and are independently aromatic organic groups, and X is a halogen, wherein the electrolyte additive is included at 0.1 to 3 wt % based on the total amount of electrolyte.

6. The rechargeable lithium battery of claim 5, wherein X is chlorine (Cl).

7. The rechargeable lithium battery of claim 5, wherein the electrolyte additive comprises a compound represented by the following Chemical Formula 2:

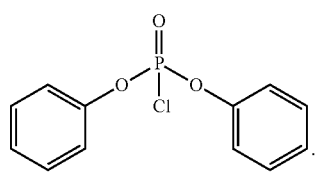

[Chemical Formula 2]

8. The rechargeable lithium battery of claim 5, wherein the electrolyte further comprises a vinylene carbonate-based compound, an ethylene carbonate-based compound represented by the following Chemical Formula 3, or a combination thereof:

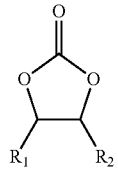

[Chemical Formula 3]

wherein, in Chemical Formula 3, $R_1$ and $R_2$ are independently selected from a group consisting of hydrogen, a halogen, a cyano group (CN), a nitro group ($NO_2$), and a C1 to C5 fluoroalkyl group, provided that both $R_1$ and $R_2$ are not hydrogen.

9. The rechargeable lithium battery of claim 5, wherein the positive active material is selected from compounds represented by the following Chemical Formulas:

$Li_aA_{1-b}X_bD_2$ ($0.90 \leq a \leq 1.8$ and $0 \leq b \leq 0.5$); $Li_aA_{1-b}X_b O_{2-c}D_c$ ($0.90 \leq a \leq 1.8$, $0 \leq b \leq 0.5$, and $0 \leq c \leq 0.05$); $Li_aE_{1-b}X_bO_{2-c}D_c$ ($0.90 \leq a \leq 1.8$, $0 \leq b \leq 0.5$ and $0 \leq c \leq 0.05$); $Li_aE_{2-b}X_bO_{4-c}D_c$ ($0.90 \leq a \leq 1.8$, $0 \leq b \leq 0.5$ and $0 \leq c \leq 0.05$); $Li_aNi_{1-b-c}2Co_bX_cD_\alpha$ ($0.90 \leq a \leq 1.8$, $0 \leq b \leq 0.5$, $0 \leq c \leq 0.05$, and $0 < \alpha < 2$); $Li_aNi_{1-b-c}Co_bX_cO_{2-\alpha}T_\alpha$ ($0.90 \leq a \leq 1.8$, $0 \leq b \leq 0.5$, $0 \leq c \leq 0.05$, and $0 < \alpha < 2$); $Li_aNi_{1-b-c}Co_bX_cO_{2-\alpha}T_2$ ($0.90 \leq a \leq 1.8$, $0 \leq b \leq 0.5$, $0 \leq c \leq 0.05$, and $0 < \alpha < 2$); $Li_aNi_{1-b-c}Mn_b X_cD_\alpha$ ($0.90 \leq a \leq 1.8$, $0 \leq b \leq 0.5$, $0 \leq c \leq 0.05$, and $0 < \alpha \leq 2$); $Li_aNi_{1-b-c}Mn_bX_cO_{2-\alpha}T_\alpha$ ($0.90 \leq a \leq 1.8$, $0 \leq b \leq 0.5$, $0 \leq c \leq 0.05$, and $0 < \alpha < 2$); $Li_aNi_{1-b-c}Mn_b X_cO_{2-\alpha}T_2$ ($0.90 \leq a \leq 1.8$, $0 \leq b \leq 0.5$, $0 \leq c \leq 0.05$, and $0 < \alpha < 2$); $Li_aNi_bE_cG_dO_2$ ($0.90 \leq a \leq 1.8$, $0 \leq b \leq 0.9$, $0 \leq c \leq 0.5$, and $0.001 \leq d \leq 0.1$); $Li_aNi_bCo_{w10\_c}Mn_dG_eO_2$ ($0.90 \leq a \leq 1.8$, $0 \leq b \leq 0.9$, $0 \leq c \leq 0.5$, $0 \leq d \leq 0.5$, and $0.001 \leq e \leq 0.1$); $Li_aNiG_bO_2$ ($0.90 \leq a \leq 1.8$ and $0.001 \leq b \leq 0.1$); $Li_aCoG_bO_2$ ($0.90 \leq a \leq 1.8$ and $0.001 \leq b \leq 0.1$); $Li_aMnG_bO_2$ ($0.90 \leq a \leq 1.8$ and $0.001 \leq b \leq 0.1$); $Li_aMn_2G_bO_4$ ($0.90 \leq a \leq 1.8$ and $0.001 \leq b \leq 0.1$); $Li_aMnG_bPO_4$ ($0.90 \leq a \leq 1.8$ and $0.001 \leq b \leq 0.1$); $QO_2$; $QS_2$; $LiQS_2$; $V_2O_5$; $LiV_2O_5$; $LiZO_2$; $LiNiVO_4$; $Li_{(3-f)}J_2(PO_4)_3$ ($0 \leq f \leq 2$); $Li_{(3-f)}Fe_2(PO_4)_3$ ($0 \leq f \leq 2$); and $LiFePO_4$, wherein, in the above Chemical Formulae, A is selected from a group consisting of Ni, Co, Mn, and a combination thereof; X is selected from a group consisting of Al, Ni, Co, Mn, Cr, Fe, Mg, Sr, V, a rare earth element, and a combination thereof; D is selected from a group consisting of O, F, S, P, and a combination thereof; E is selected from a group consisting of Co, Mn, and a combination thereof; T is selected from a group consisting of F, S, P, and a combination thereof; G is selected from a group consisting of Al, Cr, Mn, Fe, Mg, La, Ce, Sr, V, and a combination thereof; Q is selected from a group consisting of Ti, Mo, Mn, and a combination thereof; Z is selected from a group consisting of Cr, V, Fe, Sc, Y, and a combination thereof; and J is selected from a group consisting of V, Cr, Mn, Co, Ni, Cu, and a combination thereof.

10. The rechargeable lithium battery of claim 5, wherein the positive active material comprises a lithium nickel cobalt manganese-based oxide.

11. The battery of claim 5, wherein X is chlorine (Cl).

* * * * *